United States Patent
Yokosawa et al.

(10) Patent No.: US 10,550,202 B2
(45) Date of Patent: *Feb. 4, 2020

(54) HYDROXYALKYL ALKYL CELLULOSE, METHOD FOR PRODUCING THE SAME, AND SOLID PREPARATION

(71) Applicant: SHIN-ETSU CHEMICAL CO., LTD., Tokyo (JP)

(72) Inventors: Takuya Yokosawa, Joetsu (JP); Taishi Kitaguchi, Joetsu (JP); Yasuyuki Hirama, Joetsu (JP); Akira Kitamura, Joetsu (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 114 days.

This patent is subject to a terminal disclaimer.

(21) Appl. No.: 15/722,636

(22) Filed: Oct. 2, 2017

(65) Prior Publication Data

US 2018/0100028 A1 Apr. 12, 2018

(30) Foreign Application Priority Data

Oct. 7, 2016 (JP) ................... 2016-199099

(51) Int. Cl.
| | |
|---|---|
| *C08B 11/08* | (2006.01) |
| *C08B 11/02* | (2006.01) |
| *C08B 3/08* | (2006.01) |
| *G01N 15/02* | (2006.01) |
| *C08B 3/14* | (2006.01) |
| *G01N 21/47* | (2006.01) |

(52) U.S. Cl.
CPC ............... *C08B 3/08* (2013.01); *C08B 3/14* (2013.01); *G01N 15/0211* (2013.01); *G01N 2021/479* (2013.01)

(58) Field of Classification Search
CPC ............................... C08B 11/08; C08B 11/02
USPC ........................ 536/90, 91, 95, 96
See application file for complete search history.

(56) References Cited

U.S. PATENT DOCUMENTS

| 5,574,150 | A | 11/1996 | Yaginuma et al. |
| 6,235,893 | B1 | 5/2001 | Reibert et al. |
| 2015/0231082 | A1 | 8/2015 | Yokosawa et al. |

FOREIGN PATENT DOCUMENTS

| JP | H06-316535 | A | 11/1994 |
| JP | 2010523688 | A | 7/2010 |
| JP | 2010254756 | A | 11/2010 |
| JP | 2014-510137 | A | 4/2014 |
| JP | 2015166453 | A | 9/2015 |
| WO | 2008/127794 | A2 | 10/2008 |
| WO | 2012/138529 | A1 | 10/2012 |
| WO | 2012/138532 | A2 | 10/2012 |
| WO | 2014/052213 | A1 | 4/2014 |

OTHER PUBLICATIONS

Coffey et al. "Cellulose and Cellulose Derivatives." Food Polysaccharides and their Applications, Marcel Dekker, Inc., 1995.
Mar. 21, 2018 Extended European Search Report issued in European Patent Application No. 17195310.2.
Mar. 21, 2018 Extended European Search Report issued in European Patent Application No. 17195311.0.
U.S. Appl. No. 15/722,592, filed Oct. 2, 2017 in the name of Yokosawa et al.

*Primary Examiner* — Shaojia A Jiang
*Assistant Examiner* — Everett White
(74) *Attorney, Agent, or Firm* — Oliff PLC

(57) ABSTRACT

There is provided is a hydroxyalkyl alkyl cellulose exhibiting good flowability and high compressibility. More specifically, provided are a hydroxyalkyl alkyl cellulose having a volume-based average particle diameter, determined by dry laser diffractometry, of 50 to 100 μm, and having, on a basis of a dynamic image analysis to divide all particles into fine particles, spherical particles and fibrous particles, a volume fraction of the fibrous particles consisting of long and short fibrous particles relative to all of the particles of 45 to 70%, and a volume fraction of the fine particles relative to all of the particles of less than 2.0%; a solid preparation including the hydroxyalkyl alkyl cellulose; and others.

12 Claims, 2 Drawing Sheets

HYDROXYALKYL ALKYL CELLULOSE, METHOD FOR PRODUCING THE SAME, AND SOLID PREPARATION

BACKGROUND OF THE INVENTION

1. Field of the Invention

The invention relates to a hydroxyalkyl alkyl cellulose, a method for producing the hydroxyalkyl alkyl cellulose, and a solid preparation comprising the hydroxyalkyl alkyl cellulose.

2. Related Art

A sustained-release preparation enables control of the concentration of an active ingredient dissolved in the blood at a certain level or less, or reduction of the number of administrations, so that it is useful. The sustained-release preparation is roughly classified into a single unit type and a multiple unit type. The single unit type preparation gradually releases an active ingredient to exhibit sustained-release characteristics, while maintaining the dosage form thereof in the gastrointestinal tract. Examples of the single unit type preparation include a matrix type preparation that is produced by tableting a mixture containing a water-soluble polymer or a wax. The multiple unit type preparation is a tablet or a capsule that is immediately disintegrated on administration to discharge granules, wherein the granules have been produced by coating a drug with a polymer film and exhibit sustained-release characteristics.

The matrix type sustained-release preparation is produced by a simple method, and the dissolution thereof is easily controlled. Hence, the matrix type sustained-release preparation is one of the most commonly used sustained-release preparations. When the matrix type sustained-release preparation is, for example, of a gel matrix type, hydroxypropyl methyl cellulose (hereinafter also called "HPMC"), which is a water-soluble polymer, is used.

Examples of the method for producing a matrix type sustained-release preparation comprising the HPMC include a dry direct tableting method in which a mixture of a drug and the HPMC is directly subjected to tableting, and a wet granulation tableting method in which a mixture of a drug, the HPMC and an additive is granulated together with an appropriate solvent and the resulting granules are dried and then subjected to tableting. Examples of the dry direct tableting method may include, when a drug or the HPMC has insufficient flowability, a dry granulation tableting method in which a mixture after roll compression (dry granulation) is pulverized and then subjected to tableting. Examples of the wet granulation tableting method include the wet granulation tableting method with an agitation granulator and the wet granulation tableting method with a fluidized bed granulator.

The dry direct tableting method is a simple production method and thus is commonly used as the method of producing a matrix type preparation containing HPMC. The dry direct tableting method, however, requires the high content of HPMC in the preparation. Hence, when HPMC having low compressibility is used, the resulting tablet has insufficient strength and may break or crack, or tableting failures such as capping may take place during tableting.

Examples of the additive having high compressibility include crystalline cellulose (JP 06-316535A), low-substituted hydroxypropyl cellulose (JP 2010-254756A), and a hydroxyalkyl alkyl cellulose for tableting (JP 2015-166453A). The hydroxyalkyl alkyl cellulose to be contained by a sustained-release preparation is exemplified by a cellulose derivative having an average particle diameter of 150 to 800 μm (JP 2010-523688T, which is the Japanese phase publication of WO 2008/127794A) and a polysaccharide derivative having a particular particle shape (JP 2014-510137T, which is the Japanese phase publication of WO 2012/138529A).

SUMMARY OF THE INVENTION

However, the crystalline cellulose disclosed in JP 06-316535A and the low-substituted hydroxypropyl cellulose disclosed in JP 2010-254756A are water-insoluble polymers so that they fail to form a gel matrix because the surfaces thereof are not dissolved. Thus, neither of them can be used as an additive for producing a sustained-release preparation. These additives are known to have high compressibility, but also known to have disintegrability, so that they are unsuitable for the binder contained by a sustained-release preparation. Meanwhile, the hydroxyalkyl alkyl cellulose for tableting disclosed in JP 2015-166453A has a particular specific surface area and is shown to have high compressibility. However, a hydroxyalkyl alkyl cellulose having an average particle diameter of 50 μm or more is required to have further improvement of higher mixing properties or flowability during production of a sustained-release preparation.

The cellulose derivative disclosed in JP 2010-523688T has excellent flowability, but is in the form of coarse particles having a particle diameter of 150 to 800 μm, and thus has insufficient compressibility. On the other hand, the volume fraction of fibrous particles in JP 2014-510137T is 1 to 40% by volume, so that the compressibility is supposed to be relatively poor.

An object of the invention is to provide a hydroxyalkyl alkyl cellulose exhibiting good flowability and high compressibility.

As a result of intensive studies for achieving the object, the inventors have found that a hydroxyalkyl alkyl cellulose having a volume-based average particle diameter, determined by dry laser diffractometry, of 50 to 100 μm, a volume fraction of fibrous particles of 45 to 70%, the fibrous particles being total of long fibrous particles and short fibrous particles, and a volume fraction of fine particles of less than 2.0% exhibits good flowability and high compressibility, and have completed the invention.

In an aspect of the invention, there is provided a hydroxyalkyl alkyl cellulose having a volume-based average particle diameter, determined by dry laser diffractometry, of 50 to 100 μm, and having, on a basis of a dynamic image analysis to divide all particles into fine particles, spherical particles and fibrous particles, a volume fraction of the fibrous particles consisting of long and short fibrous particles relative to all of the particles of 45 to 70%, and a volume fraction of the fine particles relative to all of the particles of less than 2.0%, wherein the fine particles have a length of fiber of less than 40 μm, the spherical particles have a length of fiber of 40 μm or more and consist of first and second spherical particles, wherein the first spherical particles have an elongation, which is a ratio of a diameter of fiber to a length of fiber, of 0.5 or more, and the second spherical particles have an elongation of less than 0.5, an aspect ratio, which is a ratio of a maximal Feret diameter to a minimal Feret diameter, of 0.5 or more, and a circularity, which is a ratio of a perimeter ($P_{EQPC}$) of a circle that has the same area as a projection area to a perimeter ($P_{real}$) of a real particle, of 0.7 or more, the long fibrous particles have a length of fiber of 200 μm or more and an elongation of less than 0.5, and consist of first and second long fibrous particles, wherein the first long fibrous particles have an aspect ratio of less than 0.5, and the second long fibrous particles have an aspect ratio of 0.5 or more and a circularity of less than 0.7, and the short fibrous particles have a length of fiber of 40 μm or more and less than 200 μm and an elongation of less than 0.5, and consist of first and second short fibrous particles wherein the first short fibrous particle have an aspect ratio of less than 0.5, and the second short fibrous particle have an aspect ratio of 0.5 or more and a circularity of less than 0.7.

In another aspect of the invention, there is provided a solid preparation comprising the hydroxyalkyl alkyl cellulose.

In still another aspect of the invention, there is provided a method for producing the hydroxyalkyl alkyl cellulose, comprising the steps of: bringing cellulose pulp into contact with an alkali metal hydroxide solution to obtain alkali cellulose, reacting the alkali cellulose with an etherifying agent to obtain a hydroxyalkyl alkyl cellulose product, washing and draining the hydroxyalkyl alkyl cellulose product to obtain a first wet hydroxyalkyl alkyl cellulose, granulating the first wet hydroxyalkyl alkyl cellulose to obtain a granulated hydroxyalkyl alkyl cellulose, drying the granulated hydroxyalkyl alkyl cellulose to obtain a dried hydroxyalkyl alkyl cellulose having an average particle diameter, determined by a sieving analysis, of 2 to 10 mm and a water content of 6 to 10% by weight, mixing the dried hydroxyalkyl alkyl cellulose with water to obtain a second wet hydroxyalkyl alkyl cellulose, and drying and pulverizing the second wet hydroxyalkyl alkyl cellulose to obtain the hydroxyalkyl alkyl cellulose.

In another aspect of the invention, there is provided a method for producing a tablet, comprising each step of the method for producing the hydroxyalkyl alkyl cellulose and a step of tableting the produced hydroxyalkyl alkyl cellulose by a dry direct tableting method or a dry granulation tableting method.

According to the invention, the hydroxyalkyl alkyl cellulose exhibits good flowability and high compressibility, so that a solid preparation containing the hydroxyalkyl alkyl cellulose can provide high hardness. For this reason, for example, even the tablet containing a main drug having poor compressibility can be produced to have sufficient strength. In addition, a tablet can be produced at a low tableting pressure, so that tableting failures such as capping can be suppressed.

DETAILED DESCRIPTION OF THE PREFERRED EMBODIMENTS

Figure 1:
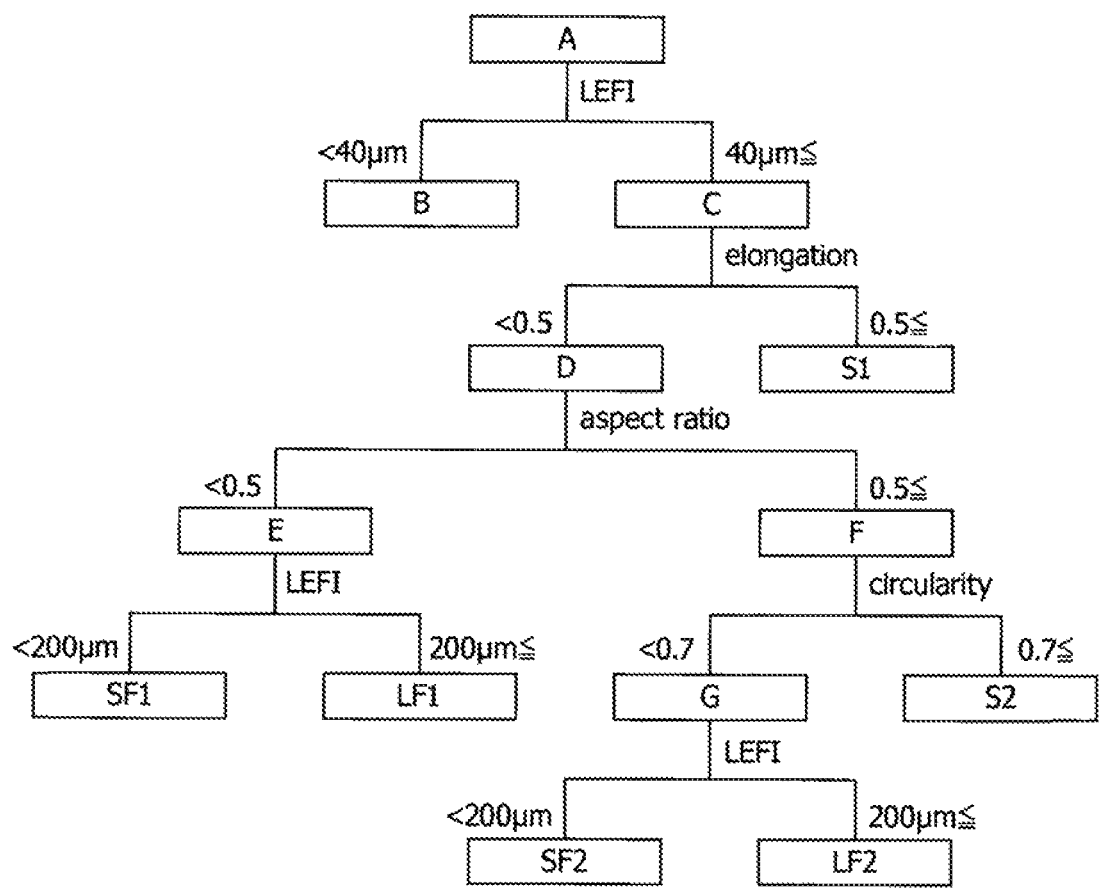
FIG. 1 is a flowchart of dividing the "all particles" of a hydroxyalkyl alkyl cellulose into four types of particles, "fine particles", "long fibrous particles (LF1 and LF2)", "short fibrous particles (SF1 and SF2)", and "spherical particles (S1 and S2)".

In the specification, a hydroxyalkyl alkyl cellulose is divided into four types of particles, "long fibrous particles", "short fibrous particles", "spherical particles", and "fine particles". FIG. 1 is a flowchart that summarizes the division of "all particles" of a hydroxyalkyl alkyl cellulose into four types of particles, "fine particles", "long fibrous particles (LF1 and LF2)", "short fibrous particles (SF1 and SF2)", and "spherical particles (S1 and S2)".

Each volume fraction of the respective types of particles of a hydroxyalkyl alkyl cellulose can be determined by measuring shape parameters including a length of fiber (LEFI), a diameter of fiber (DIFI), an elongation, an aspect ratio, and a circularity, by the dynamic image analysis. The dynamic image analysis is a method in which images of particles dispersed in a fluid such as a gas and a solvent are continuously recorded and are binarized and analyzed to obtain a particle diameter or a particle shape. The analysis can be performed by using, for example, a dynamic image analysis type particle diameter distribution analyzer, QICPIC/R16 (manufactured by Sympatec GmbH).

All particles A are divided into particles C having a length of fiber (LEFI) of 40 μm or more and fine particles B having a length of fiber of less than 40 μm. The LEFI is defined as the length of the longest direct path that connects the ends of the particle within the contour of the particle. A QICPIC/R16 equipped with an M7 lens has a detection limit of 4.7 μm and thus fails to detect a particle having an LEFI of less than 4.7 μm. However, the volume of particles having an LEFI of less than 4.7 μm is extremely small relative to that of all particles of the hydroxyalkyl alkyl cellulose so that it is negligible for the purpose of the invention.

The particles C having an LEFI of 40 μm or more are divided into first spherical particles (S1) having an elongation of 0.5 or more and particles D having an elongation of less than 0.5, wherein the elongation is a ratio of a diameter of fiber (DIFI) to LEFI (DIFI/LEFI) of the particle. The DIFI is defined as the minor diameter of a particle, and is calculated by dividing the projection area of the particle by the sum of all lengths of the fiber branches of the particle.

The particles D having an LEFI of 40 μm or more and an elongation of less than 0.5 are divided into particles E having an aspect ratio of less than 0.5 and particles F having an aspect ratio of 0.5 or more, wherein the aspect ratio is a ratio ($F_{min}/F_{max}$) of minimal Feret diameter ($F_{min}$) to maximal Feret diameter ($F_{max}$). Each particle has an aspect ratio of more than 0 and not more than 1. The Feret diameter is the distance between two parallel tangent lines that put the particle therebetween. The maximal Feret diameter ($F_{max}$) is the largest distance between pairs of tangent lines to the particle in consideration of all possible orientations by changing the directions from 0° to 180°, and the minimal Feret diameter ($F_{min}$) is a minimal distance between pairs of tangent lines to the particle in consideration of all possible orientations by changing the directions from 0° to 180°.

The fibrous particles E having an LEFI of 40 μm or more, an elongation of less than 0.5, and an aspect ratio of less than 0.5 are divided into first long fibrous particles (LF1) having an LEFI of 200 μm or more and first short fibrous particles (SF1) having an LEFI of less than 200 μm.

The particles F having an LEFI of 40 μm or more, an elongation of less than 0.5, and an aspect ratio of 0.5 or more are divided into second spherical particles (S2) having a circularity of 0.7 or more and fibrous particles G having a circularity of less than 0.7. The circularity is a ratio of the perimeter ($P_{EQPC}$) of a circle that has the same area as the projection area ($A_p$) of the particle to the perimeter ($P_{real}$) of the real particle, and is defined by the following equation. Each particle has a circularity of more than 0 and not more than 1. A particle having a smaller circularity has a more irregular shape. The EQPC is the diameter of a circle of an equal projection area, and is defined as the diameter of a circle that has the same area as the projection area of the particle, and is also called Heywood diameter.

$$\text{Circularity}=P_{EQPC}/P_{real}=2\sqrt{\pi \cdot A_P}/P_{real}$$

The fibrous particles G having an LEFI of 40 μm or more, an elongation of less than 0.5, an aspect ratio of 0.5 or more, and a circularity of less than 0.7 are divided into second long fibrous particles (LF2) having an LEFI of 200 μm or more and second short fibrous particles (SF2) having an LEFI of less than 200 μm.

The volume ($V_m$) of the fine particles of a hydroxyalkyl alkyl cellulose can be calculated by the following equation where each fine particle is assumed to be a sphere having a diameter of EQPC.

$$V_m=(\pi/6)\times(EQPC)^3\times N_m,$$

wherein $N_m$ is the number of fine particles in a sample, and EQPC is a median EQPC corresponding to the 50% cumulative value on a number-based cumulative particle diameter distribution curve of the fine particles.

In the specification, particles having an LEFI of 40 μm or more, which are particles other than the fine particles having an LEFI of less than 40 μm among the all particles, are divided, on the basis of such above shape parameters of particles as LEFI, an elongation, an aspect ratio, and a circularity, into "long fibrous particles", "short fibrous particles", and "spherical particles", which are distinguished from each other.

<Long Fibrous Particles>

Particles satisfying the following definition of LF1 or LF2 are combined into "long fibrous particles".

LF1: particles having an elongation of less than 0.5, an aspect ratio of less than 0.5, and an LEFI (length of fiber) of 200 μm or more, and LF2: particles having an elongation of less than 0.5, an aspect ratio of 0.5 or more, a circularity of less than 0.7, and an LEFI (length of fiber) of 200 μm or more.

The volume ($V_{LF}$) of the long fibrous particles of a hydroxyalkyl alkyl cellulose can be calculated by the following equation wherein each long fibrous particle is assumed to be a cylindrical column having DIFI as a bottom diameter and LEFI as a height.

$$V_{LF}=(\pi/4)\times(DIFI)^2\times(LEFI)\times N_{LF},$$

wherein $N_{LF}$ is the number of long fibrous particles in the sample, DIFI is a median DIFI corresponding to the 50% cumulative value on a number-based cumulative particle diameter distribution curve of the long fibrous particles, and LEFI is a median LEFI corresponding to the 50% cumulative value on a number-based cumulative particle diameter distribution curve of the long fibrous particles.

The volume of particles satisfying the definition LF1 and the volume of particles satisfying the definition LF2 are calculated in accordance with the above equation, respectively, and a sum of the volumes means the volume of the long fibrous particles of a hydroxyalkyl alkyl cellulose.

<Short Fibrous Particles>

Particles satisfying the following definition of SF1 or SF2 are combined into "short fibrous particles".

SF1: particles having an elongation of less than 0.5, an aspect ratio of less than 0.5, and an LEFI (length of fiber) of not less than 40 μm and less than 200 μm, and SF2: particles having an elongation of less than 0.5, an aspect ratio of 0.5 or more, a circularity of less than 0.7, and an LEFI (length of fiber) of not less than 40 μm and less than 200 μm.

The volume ($V_{SF}$) of the short fibrous particles of a hydroxyalkyl alkyl cellulose can be calculated by the following equation where each short fibrous particle is assumed to be a cylindrical column having a bottom diameter of DIFI and a height of LEFI, in the same manner as for the above long fibrous particles.

$$V_{SF}=(\pi/4)\times(DIFI)^2\times(LEFI)\times N_{SF},$$

wherein $N_{SF}$ is the number of short fibrous particles in the sample, DIFI is a median DIFI corresponding to the 50% cumulative value on a number-based cumulative particle diameter distribution curve of the short fibrous particles, and LEFI is a median LEFI corresponding to the 50% cumulative value on a number-based cumulative particle diameter distribution curve of the short fibrous particles.

The volume of particles satisfying the definition of SF1 and the volume of particles satisfying the definition of SF2 are calculated in accordance with the above equation, respectively, and a sum of the volumes means the volume of the short fibrous particles of a hydroxyalkyl alkyl cellulose.

<Spherical Particles>

Particles satisfying the definition of S1 or S2 are combined into "spherical particles".

S1: particles having an elongation of 0.5 or more and an LEFI (length of fiber) of 40 μm or more, and S2: particles having an elongation of less than 0.5, an aspect ratio of 0.5 or more, a circularity of 0.7 or more, and an LEFI (length of fiber) of 40 μm or more.

The volume ($V_S$) of the spherical particles of a hydroxyalkyl alkyl cellulose can be calculated by the following equation where each spherical particle is assume to be a sphere having a diameter of EQPC.

$$V_S=(\pi/6)\times(EQPC)^3\times N_S,$$

wherein $N_S$ is the number of spherical particles in the sample, and EQPC is a median EQPC corresponding to the 50% cumulative value on a number-based cumulative particle diameter distribution curve of the spherical particles.

The volume of particles satisfying the definition S1 and the volume of particles satisfying the definition S2 are calculated in accordance with the above equation, respectively, and a sum of the volumes means the volume of the spherical particles of a hydroxyalkyl alkyl cellulose.

The volume fraction of each type of particles of a hydroxyalkyl alkyl cellulose can be calculated from the following corresponding equation on basis of the above-defined volumes, $V_m$, $V_{LF}$, $V_{SF}$, and $V_S$.

Volume fraction of fine particles=$\{V_m/(V_m+V_{LF}+V_{SF}+V_S)\}\times 100$

Volume fraction of long fibrous particles=$\{V_{LF}/(V_m+V_{LF}+V_{SF}+V_S)\}\times 100$ Volume fraction of short fibrous particles=$\{V_{SF}/(V_m+V_{LF}+V_{SF}+V_S)\}\times 100$ Volume fraction of spherical particles=$\{V_S/(V_m+V_{LF}+V_{SF}+V_S)\}\times 100$ The hydroxyalkyl alkyl cellulose has a volume-based average particle diameter, determined by dry laser diffractometry, of 50 to 100 μm, preferably 60 to 90 μm, more preferably 65 to 90 μm, and even more preferably 65 to 85 μm.

The volume-based average particle diameter can be determined by dry laser diffractometry. For example, the volume-based average particle diameter can be determined by a method using MASTERSIZER 3000 manufactured by Malvern Instrument Ltd in England or HELOS manufactured by Sympatec GmbH in Germany, where a laser beam is applied to a powder sample sprayed by compressed air to measure diffraction intensities, which are used to obtain the volume-based average particle diameter.

In the specification, the volume-based average particle diameter was determined by using a laser diffraction particle diameter analyzer MASTERSIZER 3000 (manufactured by Malvern Instrument Ltd) based on the Fraunhofer diffraction theory in conditions of a dispersion pressure of 2 bar and a scattering intensity of 2 to 10%, as a particle diameter corresponding to the 50% cumulative value on a volume-based cumulative particle diameter distribution curve.

The hydroxyalkyl alkyl cellulose has a volume fraction of fibrous particles of 45 to 70%, preferably 47 to 65%, more preferably 49% to 60%, wherein the fibrous particles are the total of long and short fibrous particles. When a hydroxyalkyl alkyl cellulose having a volume-based average particle diameter, determined by dry laser diffractometry, of 50 μm to 100 μm has a volume fraction of fibrous particles of less than 45%, the hydroxyalkyl alkyl cellulose may have poor compressibility. When a hydroxyalkyl alkyl cellulose having a volume-based average particle diameter, determined by dry laser diffractometry, of 50 μm to 100 μm has a volume fraction of fibrous particles of more than 70%, the hydroxyalkyl alkyl cellulose may have poor flowability for tableting or have poor mixing properties with another powder.

The hydroxyalkyl alkyl cellulose has a volume fraction of fine particles of less than 2.0%, preferably less than 1.5%, more preferably less than 1.3%. When the volume fraction of fine particles is 2.0% or more, good flowability may not be obtained.

Fine particles commonly have a high specific surface area so that a hydroxyalkyl alkyl cellulose containing a large number of fine particles is considered to have high compressibility, although the flowability becomes poor. However, according to the invention, it has been found that the hydroxyalkyl alkyl cellulose having a volume fraction of fine particles of as small as less than 2.0% can have high compressibility when it has a volume fraction of fibrous particles of 45 to 70%, wherein the fibrous particles are the total of long and short fibrous particles.

The hydroxyalkyl alkyl cellulose has a volume fraction of the short fibrous particles of preferably 15 to 35%, more preferably 15 to 32%, even more preferably 17 to 32%, particularly preferably 20 to 30% from the standpoint of good flowability and high compressibility.

The hydroxyalkyl alkyl cellulose has a volume fraction ratio of the short fibrous particles to the long fibrous particles (short fibrous particles/long fibrous particles) of preferably 0.60 to 1.40, more preferably 0.60 to 1.30, even more preferably 0.60 to 1.20 from the standpoint of good flowability and high compressibility.

The hydroxyalkyl alkyl cellulose has a volume fraction of the spherical particles of preferably 30% or more, more preferably 35% or more, even more preferably 40% or more from the standpoint of good flowability. The upper limit of the volume fraction of the spherical particles is not particularly limited, and is preferably less than 60% from the standpoint of high compressibility.

The hydroxyalkyl alkyl cellulose has a specific surface area, determined by BET method (multipoint BET method), of preferably not less than 0.35 $m^2/g$ and less than 0.50 $m^2/g$, more preferably 0.40 to 0.49 $m^2/g$, even more preferably 0.41 to 0.49 $m^2/g$ from the standpoint of good flowability and high compressibility. A powder having a large specific surface area is generally known to have high compressibility. However, according to the invention, it has been found that the hydroxyalkyl alkyl cellulose having a specific surface area of as small as 0.30 to 0.50 $m^2/g$ can have high compressibility when it has a volume fraction of fibrous particles of 45% to 70%, wherein the fibrous particles are the total of long and short fibrous particles.

The specific surface area can be determined by the BET method (multipoint BET method), which is based on low-temperature low-humidity physical adsorption of an inert gas and is a method in which the surfaces of sample powder particles are allowed to adsorb molecules at the temperature of liquid nitrogen and the specific surface area of the sample can be determined from the amount of molecules adsorbed because the area occupied by the unit amount of molecules through adsorption is known. For example, the specific surface area can be determined in accordance with "Method 2: The volumetric method", in "Specific Surface Area by Gas Adsorption" under "General Tests" described in the Japanese Pharmacopoeia Seventeenth Edition, by using an automatic specific surface area/pore distribution analyzer TriStar II 3020 (manufactured by Micromeritics Instrument Corp.). Specifically, the specific surface area was determined by gas adsorption method (adsorption gas: krypton, and refrigerant: liquid nitrogen) within a relative pressure ($P/P_0$) of 0.05 to 0.30 wherein $P_0$ is a saturated vapor pressure, and P is a measured equilibrium pressure). A measurement sample was allowed to stand at 105° C. for 2 hours to be absolutely dried in advance and was used. The sample amount varies depending on measurement samples, and 1.0 to 2.0 g of a sample can be subjected to the measurement.

The viscosity at 20° C. of a 2% by weight aqueous solution of the hydroxyalkyl alkyl cellulose is preferably 50 to 200,000 mPa·s, more preferably 100 to 170,000 mPa·s, even more preferably 4,000 to 170,000 mPa·s, particularly preferably 4,000 to 100,000 mPa·s from the standpoint of, for example, control of the dissolution of a drug from a sustained release preparation.

The viscosity at 20° C. of a 2% by weight aqueous solution can be determined in accordance with "Viscosity measurement by rotational viscometer" in "Viscosity Determination" under "General Tests" described in the Japanese Pharmacopoeia Seventeenth Edition, by using a single cylinder-type rotational viscometer, when the 2% by weight aqueous solution has a viscosity of 600 mPa·s or more. When the 2% by weight aqueous solution has a viscosity of less than 600 mPa·s, the viscosity can be determined in accordance with "Viscosity measurement by capillary tube viscometer" in "Viscosity Determination" under "General Tests" described in the Japanese Pharmacopoeia Seventeenth Edition, by using an Ubbelohde-type viscometer.

The hydroxyalkyl alkyl cellulose is a nonionic water-soluble polymer produced by etherification of some hydroxy groups on a glucose ring of cellulose. Examples of the hydroxyalkyl alkyl cellulose include, but not limited to, hydroxypropyl methyl cellulose and hydroxyethyl methyl cellulose. The hydroxypropyl methyl cellulose (HPMC) is particularly preferable from the standpoint of, for example, control of the dissolution of a drug from a sustained-release preparation.

The substitution degrees of the hydroxyalkyl alkyl cellulose are not particularly limited. For example, with respect to hydroxypropyl methyl cellulose, the substitution degree of methoxy group is preferably 16.5 to 30.0% by weight, more preferably 19.0 to 30.0% by weight, even more preferably 19.0 to 24.0% by weight, while the substitution degree of hydroxypropoxy group is preferably 3.0 to 32.0% by weight, more preferably 3.0 to 12.0% by weight, even more preferably 4.0 to 12.0% by weight, particularly preferably 8.5 to 10.5% by weight. These substitution degrees can be determined by a method in accordance with the measurement method of substitution degree for hydroxypropyl methyl cellulose (hypromellose) described in the Japanese Pharmacopoeia Seventeenth Edition.

Next, a method for producing the hydroxyalkyl alkyl cellulose will be described.

The hydroxyalkyl alkyl cellulose can be produced by a method comprising the steps of: bringing cellulose pulp into contact with an alkali metal hydroxide solution to obtain alkali cellulose, and reacting the alkali cellulose with an etherifying agent for etherification to obtain a crude hydroxyalkyl alkyl cellulose as the reaction product.

Examples of the cellulose pulp include wood pulp and linter pulp. The cellulose pulp may be in the form of sheet, chips, or powder. The cellulose pulp in a chip form or a powder form is preferable from the standpoint of enhancement of the stirring efficiency in a reactor. The intrinsic viscosity of the cellulose pulp is not particularly limited, and is preferably 200 to 2,500 mL/g. The intrinsic viscosity of the cellulose pulp can be determined by a method in accordance with the viscosity measurement method in JIS (Japanese Industrial Standards) P8215.

The alkali metal hydroxide is not particularly limited, and is preferably sodium hydroxide from the standpoint of economy.

In the etherification step, an alkali metal hydroxide solution and an etherifying agent may be present together so that the formed alkali cellulose can be immediately reacted with the etherifying agent. Alternatively, after the formation of alkali cellulose, an etherifying agent can be introduced to react with the alkali cellulose. The etherifying agent useful for producing the hydroxyalkyl alkyl cellulose product (i.e. the crude hydroxyalkyl alkyl cellulose) is not particularly limited. Examples of the etherifying agent include alkyl halides such as methyl chloride, and alkylene oxides such as ethylene oxide and propylene oxide.

The hydroxyalkyl alkyl cellulose product is subjected to a washing and draining step to give a first wet hydroxyalkyl alkyl cellulose. In the washing and draining step, washing and draining may be carried out separately or simultaneously. For example, washing may be carried out before filtering or squeezing, or washing water is poured during filtering or squeezing.

The washing and the draining can be carried out by using a known technique. For example, preferably water, more preferably hot water of preferably 85 to 100° C., is added to the hydroxyalkyl alkyl cellulose product to obtain a slurry containing the hydroxyalkyl alkyl cellulose at a concentration of preferably 1 to 15% by weight, and the slurry is drained and optionally squeezed.

Examples of the device for draining may include a vacuum filtration device, a pressure filtration device, a centrifugal dehydrator, and a filter press. Examples of the device for squeezing may include substantially the same devices as those for draining. Optionally, hot water is allowed to successively pass through the drained product for further washing; or a filtered or squeezed product may be made into a slurry once again, and the slurry may be subjected to draining or squeezing.

The obtained first wet hydroxyalkyl alkyl cellulose is granulated in a stirring mixer equipped with a stirring blade. The first wet hydroxyalkyl alkyl cellulose may be brought into contact with water in the stirring mixer. In order to reduce the load in the subsequent drying step, the amount of water to be brought into contact is preferably a minimum amount. In other word, the difference between the water content of granulated hydroxyalkyl alkyl cellulose after granulation and the water content of the first wet hydroxyalkyl alkyl cellulose before granulation is preferably 5% by weight or less, or 0% (no contact with water).

The temperature of a jacket of the stirring mixer with a stirring blade is preferably 0 to 20° C., the temperature of the hydroxyalkyl alkyl cellulose during granulation is preferably 0 to 20° C., the circumferential speed of the stirring blade is preferably 0.5 to 20 m/s, and the mixing time with stirring is preferably 1 to 60 minutes.

The mixing with stirring is carried out in such a manner as to obtain a granulated hydroxyalkyl alkyl cellulose having an average particle diameter, determined by a sieving analysis, of a predetermined range (for example, preferably 2 to 15 mm, more preferably 3 to 10 mm). For example, the granulated hydroxyalkyl alkyl cellulose may be taken out of the stirring mixer every certain time for optional control of the mixing time with stirring. The average particle diameter by a sieving analysis can be determined in accordance with the dry mechanical sieving of "Test methods for sieving of chemical products" in JIS K0069.

The granulated hydroxyalkyl alkyl cellulose is dried to obtain a dried hydroxyalkyl alkyl cellulose. The dried hydroxyalkyl alkyl cellulose preferably has an average particle diameter, determined by a sieving analysis, of 2 to 10 mm, more preferably 2 to 8 mm, even more preferably 2 to 6 mm from the standpoint of controlling the volume fraction of fibrous particles of the final hydroxyalkyl alkyl cellulose product as well as good flowability and high compressibility thereof.

The average particle diameter by the sieving analysis can be determined in accordance with the dry mechanical sieving of "Test methods for sieving of chemical products" in JIS K0069.

The dried hydroxyalkyl alkyl cellulose has a water content of 6 to 10% by weight, preferably 6 to 9% by weight, more preferably 6 to 8% by weight from the standpoint of good flowability and high compressibility of the hydroxyalkyl alkyl cellulose having a volume-based average particle diameter, determined by dry laser diffractometry, of 50 to 100 μm. By allowing the dried hydroxyalkyl alkyl cellulose to keep a certain water content, the fraction of fibrous particles, especially the fraction of short fibrous particles of the final hydroxyalkyl alkyl cellulose product can be controlled.

The water content of the dried hydroxyalkyl alkyl cellulose is defined as {(total weight of dried hydroxyalkyl alkyl cellulose—absolutely dry weight of dried hydroxyalkyl alkyl cellulose)/(total weight of dried hydroxyalkyl alkyl cellulose)}×100%.

The term "total weight of dried hydroxyalkyl alkyl cellulose" is the accurately measured weight of the dried hydroxyalkyl alkyl cellulose in accordance with "Loss on Drying Test" in the Japanese Pharmacopoeia Seventeenth Edition. The term "absolutely dry weight of dried hydroxyalkyl alkyl cellulose" is the weight reached after further drying the dried hydroxyalkyl alkyl cellulose in accordance with "Loss on Drying Test" in the Japanese Pharmacopoeia Seventeenth Edition.

Examples of the dryer may include, but not limited to, a fluidized bed dryer, a drum dryer, and an air dryer. The drying temperature is preferably 40 to 100° C., and the drying time is preferably within 10 hours, from the standpoint of suppressing discoloration of the dried cellulose ether.

The dried hydroxyalkyl alkyl cellulose is mixed with a predetermined amount of water with stirring in a stirring mixer. The water content of the second wet hydroxyalkyl alkyl cellulose varies depending on the viscosity at 20° C. of a 2% by weight aqueous solution of the final hydroxyalkyl alkyl cellulose product. Specifically, when the viscosity at 20° C. of a 2% by weight aqueous solution of a hydroxyalkyl alkyl cellulose is 50 to 10,000 mPa·s as a low-viscosity product, the water content is preferably more than 6% by weight and not more than 47% by weight, more preferably 10 to 47% by weight, even more preferably 15 to 47% by weight from the standpoint of controlling the volume fraction of fibrous particles of the final hydroxyalkyl alkyl cellulose product. When the viscosity at 20° C. of a 2% by weight aqueous solution of a hydroxyalkyl alkyl cellulose is more than 10,000 mPa·s and not more than 200,000 mPa·s as a high-viscosity product, the water content is preferably more than 47% by weight and not more than 65% by weight, more preferably 49 to 63% by weight, even more preferably 48 to 60% by weight from the standpoint of controlling the volume fraction of fibrous particles of the final hydroxyalkyl alkyl cellulose product.

The water content of the second wet hydroxyalkyl alkyl cellulose is defined as {(total weight of second wet hydroxyalkyl alkyl cellulose—absolute dry weight of second wet hydroxyalkyl alkyl cellulose)/(total weight of second wet hydroxyalkyl alkyl cellulose)}×100%.

The term "total weight of second wet hydroxyalkyl alkyl cellulose" is the accurately measured weight of the second wet hydroxyalkyl alkyl cellulose in accordance with "Loss on Drying Test" in the Japanese Pharmacopoeia Seventeenth Edition. The "absolute dry weight of second wet hydroxyalkyl alkyl cellulose" is the weight reached after drying the second wet hydroxyalkyl alkyl cellulose in accordance with "Loss on Drying Test" in the Japanese Pharmacopoeia Seventeenth Edition.

The water to be mixed with the dried hydroxyalkyl alkyl cellulose in a stirring mixer is preferably, continuously supplied into the stirring mixture from the standpoint of uniform distribution of the water among particles of the second wet hydroxyalkyl alkyl cellulose to be obtained. As the method of continuously supplying the water, for example, dropwise addition or spraying through an inlet or into the inside of the stirring mixer may be applied. The dropwise addition or spraying can be carried out at a single position or at two or more positions.

The temperature of the water to be supplied to the stirring mixer is preferably 0 to 30° C., more preferably 0 to 20° C., even more preferably 5 to 20° C., particularly preferably 5 to 15° C. from the standpoint of accelerating the dissolution of the second wet hydroxyalkyl alkyl cellulose. From the same standpoint, a fluid (preferably water) having the same temperature as that of the water to be supplied to the stirring mixer is preferably supplied to a jacket of the stirring mixer for cooling the mixture being stirred.

The staying time of the second wet hydroxyalkyl alkyl cellulose in the stirring mixer is preferably 1 to 30 minutes, more preferably 5 to 25 minutes, even more preferably 10 to 20 minutes from the standpoint of controlling the volume fraction of fibrous particles by limiting the dissolution of the second wet hydroxyalkyl alkyl cellulose to only the particle surfaces to prevent the water from infiltrating into the particles.

The circumferential speed of the stirring mixer is not particularly limited, and is preferably 0.05 to 150 m/s, more preferably 0.1 to 20 m/s, even more preferably 0.2 to 10 m/s.

As described above, by selecting the conditions of hardly dissolving the inner parts of the particles of the second wet hydroxyalkyl alkyl cellulose but preferentially dissolving only the surfaces thereof, the volume fraction of fibrous particles of the final hydroxyalkyl alkyl cellulose product can be controlled, and the fibrous particles and spherical particles are present in an appropriate balance. Hence, a hydroxyalkyl alkyl cellulose exhibiting good flowability and high compressibility can be obtained.

As the stirring mixer, a known device can be used. Examples of the stirring mixer include a ribbon mixer, a screw mixer, a rotor mixer with pins, a paddle mixer, a mixer with paddles, and a proshear mixer.

The second wet hydroxyalkyl alkyl cellulose may be dried by a known method before pulverized, or may be dried and pulverized concurrently. For example, a heated gas is introduced into an impact pulverizer together with the wet hydroxyalkyl alkyl cellulose for concurrently drying and pulverizing the wet hydroxyalkyl alkyl cellulose. Examples of the impact pulverizer include Ultra ROTOR (manufactured by Altenburger Maschinen Jäckering GmbH), TURBO MILL (manufactured by Turbo Corporation), and Victory Mill (manufactured by Hosokawa Micron Corporation).

Next, a solid preparation comprising the hydroxyalkyl alkyl cellulose will be described.

The hydroxyalkyl alkyl cellulose may be used as an additive for a solid preparation such as a tablet, a granule, a fine granule and a capsule. In particular, the hydroxyalkyl alkyl cellulose can control the dissolution of an active ingredient in a sustained-release preparation and is particularly useful as a matrix base material or a filler for the tablet, which is most commonly used because of ease of handling. The tablet may be produced by any one of the dry direct tableting method, the wet agitation-granulation tableting method, the fluidized bed granulation tableting method, and the dry granulation tableting method. Particularly, the dry direct tableting method or the dry granulation tableting method is preferable because it is a simple production process, and it can simplify the production steps for greatly reducing the production cost as compared with the wet agitation-granulation tableting method and other methods.

The granules and the fine granules are granulated products obtained by granulating a mixture containing the hydroxyalkyl alkyl cellulose and a drug. The capsules may be produced by encapsulating the granules or the fine granules.

When the hydroxyalkyl alkyl cellulose is used to produce a sustained-release preparation, the content of the hydroxyalkyl alkyl cellulose in a solid preparation is preferably 2 to 60% by weight, more preferably 10 to 50% by weight, even more preferably 20 to 40% by weight from the standpoint of, for example, controlling the dissolution of a drug from the sustained-release preparation.

According to the invention, the hydroxyalkyl alkyl cellulose has high compressibility so that it is particularly useful when the drug contained in a sustained-release preparation has poor compressibility or the drug content is large.

Next, a method for producing the solid preparation comprising the obtained hydroxyalkyl alkyl cellulose will be described.

The solid preparation may be produced by the method comprising the steps of: mixing the hydroxyalkyl alkyl cellulose with a drug and a various optional additive commonly used in the field, such as the other filler, a disintegrant, a binder, an aggregation inhibitor, and a solubilizing agent for the medical compound; and tableting or granulating the resulting mixture.

The drug to be used for producing a solid preparation comprising the hydroxyalkyl alkyl cellulose in accordance with the invention is not particularly limited insofar as it is orally administrable. Examples of the drug include a central nervous system drug, a circulatory system drug, a respiratory system drug, a digestive system drug, an antibiotic, an antitussive and expectorant drug, an antihistamine drug, an antipyretic, analgesic and anti-inflammatory drug, a diuretic drug, an autonomic drug, an antimalarial drug, an anti-diarrheal drug, a psychotropic drug, and vitamins and derivatives thereof.

Examples of the central nervous system drug include diazepam, idebenone, naproxen, piroxicam, indomethacin, sulindac, lorazepam, nitrazepam, phenytoin, acetaminophen, ethenzamide, ketoprofen, and chlordiazepoxide.

Examples of the circulatory system drug include molsidomine, vinpocetine, propranolol, methyldopa, dipyridamole, furosemide, triamterene, nifedipine, atenolol, spironolactone, metoprolol, pindolol, captopril, isosorbide nitrate, delapril hydrochloride, meclofenoxate hydrochloride, diltiazem hydrochloride, etilefrine hydrochloride, digitoxin, and alprenolol hydrochloride.

Examples of the respiratory system drug include amlexanox, dextromethorphan, theophylline, pseudoephedrine, salbutamol, and guaifenesin.

Examples of the digestive system drug include a benzimidazole-based drug having an anti-ulcer action such as 2-[[3-methyl-4-(2,2,2-trifluoroethoxy)-2-pyridyl]methylsulfinyl]benzimidazole and 5-methoxy-2-[(4-methoxy-3,5-dimethyl-2-pyridyl)methylsulfinyl]benzimidazole; cimetidine; ranitidine; pirenzepine hydrochloride; pancreatin; bisacodyl; and 5-aminosalicyclic acid.

Examples of the antibiotic include talampicillin hydrochloride, bacampicillin hydrochloride, cefaclor, and erythromycin.

Examples of the antitussive and expectorant drug include noscapine hydrochloride, carbetapentane citrate, isoaminile citrate, and dimemorfan phosphate.

Examples of the antihistamine drug include chlorpheniramine maleate, diphenhydramine hydrochloride, and promethazine hydrochloride.

Examples of the antipyretic, analgesic and anti-inflammatory drug include ibuprofen, diclofenac sodium, flufenamic acid, sulpyrine, aspirin, and ketoprofen.

Examples of the diuretic drug include caffeine.

Examples of the autonomic drug include dihydrocodeine phosphate, dl-methylephedrine hydrochloride, atropine sulfate, acetylcholine chloride, and neostigmine.

Examples of the antimalarial drug include quinine hydrochloride.

Examples of the anti-diarrheal drug include loperamide hydrochloride.

Examples of the psychotropic drug include chlorpromazine.

Examples of the vitamins and derivatives thereof include Vitamin A, Vitamin B1, fursultiamine, Vitamin B2, Vitamin B6, Vitamin B12, Vitamin C, Vitamin D, Vitamin E, Vitamin K, calcium pantothenate, and tranexamic acid.

The solid preparation may comprise an optional additive such as the other filler, a binder, a disintegrant, a lubricant, an aggregation inhibitor, a solubilizing agent for the medical compound. The content of such an additive is not particularly limited, and is preferably 1% or more and less than 98% from the standpoint of controlling the dissolution of a drug.

Examples of the other filler include a saccharide such as white sugar, lactose and glucose; sugar alcohols such as mannitol, sorbitol and erythritol; starch; crystalline cellulose; calcium phosphate; and calcium sulfate.

Examples of the binder include polyvinyl alcohol, polyacrylic acid, polymethacrylic acid, polyvinylpyrrolidone, glucose, white sugar, lactose, maltose, dextrin, sorbitol, mannitol, macrogols, gum arabic, gelatin, agar, starch, crystalline cellulose, and low-substituted hydroxypropyl cellulose.

Examples of the disintegrant include low-substituted hydroxypropyl cellulose, carmellose or a salt thereof, croscarmellose sodium, sodium carboxymethyl starch, crospovidone, crystalline cellulose, and crystalline cellulose/carmellose sodium.

Examples of the lubricant and the aggregation inhibitor include talc, magnesium stearate, calcium stearate, colloidal silica, stearic acid, waxes, hardened oil, polyethylene glycols, and sodium benzoate.

Examples of the solubilizing agent for a medical compound include organic acids such as fumaric acid, succinic acid, malic acid and adipic acid.

When the solid preparation is a tablet, examples of the method for producing the solid preparation include the dry direct tableting method, the dry granulation tableting method, the wet agitation-granulation tableting method, and the fluidized bed granulation tableting method. It is preferable to use the dry direct tableting method or the dry granulation tableting method, where the hydroxyalkyl alkyl cellulose is used without dissolution.

The dry direct tableting method is a method of tableting a mixture obtained by dry-mixing a hydroxyalkyl alkyl cellulose, a drug and an optional additive such as an filler, a disintegrant and a lubricant. The dry direct tableting method comprises no granulation step and can simplify the production process, thereby achieving high productivity.

The dry granulation tableting method is a method of tableting the product obtained by compression-granulation of a hydroxyalkyl alkyl cellulose, drug and an optional additive such as an filler, a disintegrant and a lubricant. The dry granulation tableting method is effective for a drug susceptible to water or a solvent. The compression-granulated product can be obtained by roller compression with a compaction granulator such as a roller compactor. The roll pressure varies depending on powder properties and the like, and is preferably 1 to 30 MPa, more preferably 2 to 12 MPa. The rotation speed of a roll is preferably 1 to 50 rpm, more preferably 2 to 20 rpm. The rotation speed of a screw is preferably 1 to 100 rpm, more preferably 2 to 50 rpm. Flakes of a compression-granulated product obtained by roller compression can be pulverized and sized with a pulverizer or crusher such as Comil, Quick Mill, Power Mill, Granumeister, and Roll Granulator into a powder having an intended particle diameter distribution, which will be tableted.

EXAMPLES

The invention will next be described specifically with reference to Examples and Comparative Examples. It should not be construed that the invention is limited to or by Examples.

Example 1

In a pressure vessel with an internal stirrer, 11.5 kg of a 49% by weight aqueous sodium hydroxide solution was added to 8.0 kg of powder pulp being derived from wood and having an intrinsic viscosity of 600 mL/g to obtain alkali cellulose. The alkali cellulose was subjected to addition of 9.2 kg of methyl chloride for methoxy group substitution and 2.4 kg of propylene oxide for hydroxypropoxy substitution, and reacted to obtain a HPMC product (i.e. crude HPMC). The HPMC product was then dispersed in hot water of 90° C., and drained and washed to obtain first wet HPMC.

The first wet HPMC was placed in a proshear mixer being equipped with an internal stirring blade, having a jacket temperature of 5° C., and being driven at a circumferential speed of the tip of the stirring blade of 1.6 m/s, and was granulated with stirring. The resulting granulated HPMC was dried by an air dryer at 80° C. for 6 hours. The dried HPMC had an average particle diameter, determined by a sieving analysis, of 2.5 mm and a water content of 6% by weight, as shown in Table 1.

The dried HPMC was successively introduced into a proshear mixer being equipped with a spray nozzle, having a jacket temperature of 5° C., and being driven at a circumferential speed of the tip of the stirring blade of 1.6 m/s. At the same time, water of 20° C. was continuously supplied from the spray nozzle so as to make a water content of the HPMC to be 18.0% by weight. The dried HPMC and the water was mixed with stirring for a staying time in the mixer of 20 minutes to obtain second wet HPMC.

The second wet HPMC was introduced into an impact type pulverizer Ultra ROTOR II S (manufactured by Altenburger Maschinen Jäckering GmbH) supplied with nitrogen gas of 90° C. and driven at a circumferential speed of the tip of a pulverization blade of 108 m/s, and was dried and pulverized.

The obtained HPMC had a methoxy group substitution degree of 23.5% by weight and a hydroxypropoxy group substitution degree of 9.3% by weight, and a viscosity at 20° C. of a 2% by weight aqueous solution of the obtained HPMC was 8,100 mPa·s.

Next, the obtained HPMC was subjected to measurement of the various physical properties shown below, and the results are shown in Table 2.

<Measurement of Average Particle Diameter>

The average particle diameter was determined with a laser diffraction particle diameter analyzer MASTERSIZER 3000 (manufactured by Malvern Instrument Ltd) by the dry method based on the Fraunhofer diffraction theory in conditions of a dispersion pressure of 2 bar and a scattering intensity of 2 to 10%, as a particle diameter corresponding to the 50% cumulative value on a volume-based cumulative particle diameter distribution curve.

<Measurement of Volume Fractions of Various Types of Particles>

The volume fractions of various types of particles (long fibrous particles, short fibrous particles, spherical particles and fine particles) were determined by a dynamic image analysis system particle diameter distribution analyzer QICPIC/R16 (manufactured by Sympatec GmbH) equipped with a quantitative feeder VIBRI/L, a dry disperser RODOS/L, and an M7 lens, in the following procedure. The measurement was made in conditions of a frame rate of 500 Hz, an injector of 4 mm, and a dispersion pressure of 1 bar. Then the recorded particle image was analyzed by an analysis software WINDOX5, Version: 5.9.1.1, to determine the number-based median EQPCs, the number-based median LEFIs, the number-based median DIFIs, the elongations, the aspect ratios, and the circularities, with respect to the various types of particles. The volume fractions were calculated from the determined values in accordance with the above-described equations. The division used during the analysis was M7.

<Measurement of BET Specific Surface Area>

The specific surface area by the BET method (multipoint BET method) was determined in accordance with "Method 2: The volumetric method" in "Specific Surface Area by Gas Adsorption" under "General Tests" described in the Japanese Pharmacopoeia Seventeenth Edition, with an automatic specific surface area/pore distribution analyzer TriStar II 3020 (manufactured by Micromeritics Instrument Corp.) by the gas adsorption method (adsorption gas: krypton, and refrigerant: liquid nitrogen) within a relative pressure ($P/P_0$) of 0.05 to 0.30 wherein $P_0$ is a saturated vapor pressure, and P is a measured equilibrium pressure. Measurement samples were allowed to stand at 105° C. for 2 hours to be absolutely dried in advance and were used. The sample amount varied depending on measurement samples, and 1.0 to 2.0 g of a sample was subjected to the measurement.

<Measurement of Viscosity of 2% by Weight Aqueous Solution>

The viscosity at 20° C. of a 2% by weight aqueous solution of HPMC was determined in accordance with "Viscosity measurement by rotational viscometer" in "Viscosity Determination" under "General Tests" described in the Japanese Pharmacopoeia Seventeenth Edition, with a single cylinder-type rotational viscometer.

<Measurement of Compressibility>

The compressibility was determined in the following procedure. HPMC was stored in a desiccator of 25° C., containing a saturated aqueous solution of magnesium chloride and having a relative humidity of about 33%, for 4 days so as to have a water content of 3 to 4% by weight. Then the HPMC was compression-molded by using a desktop tablet press machine HANDTAB 200 (manufactured by ICHI-HASHI SEIKI) with a flat round pestle having a diameter of 12 mm, at a tableting pressure of 10 kN (about 88.5 MPa) to obtain a 450-mg tablet. The hardness of the tablet was determined with a tablet hardness tester TBH-125 (manufactured by ERWEKA GmbH) by applying a load at a speed of 1 mm/sec in a diameter direction of the tablet, as a maximum breaking strength when the tablet was broken.

Example 2

HPMC was produced in the same manner as in Example 1 except that the production conditions were changed as shown in Table 1. The various physical properties of the obtained HPMC were determined in the same manner as in Example 1, and the results are shown in Table 2.

Example 3

HPMC was produced in the same manner as in Example 1 except that the production conditions were changed as shown in Table 1. The various physical properties of the obtained HPMC were determined in the same manner as in Example 1, and the results are shown in Table 2.

Example 4

Dried HPMC was produced in the same manner as in Example 1 except that a powder pulp being derived from wood and having an intrinsic viscosity of 1,800 mL/g was used. The dried HPMC had an average particle diameter, determined by a sieving analysis, of 3.5 mm and a water content of 7% by weight.

HPMC was produced in the same manner as in Example 1 except that water of 20° C. was continuously supplied to the dried HPMC to obtain second wet HPMC having a water content of 49% by weight. The various physical properties of the obtained HPMC were determined in the same manner as in Example 1, and the results are shown in Table 2.

Example 5

HPMC was produced in the same manner as in Example 4 except that the production conditions were changed as shown in Table 1. The various physical properties of the obtained HPMC were determined in the same manner as in Example 1, and the results are shown in Table 2.

Example 6

HPMC was produced in the same manner as in Example 4 except that the production conditions were changed as shown in Table 1. The various physical properties of the obtained HPMC were determined in the same manner as in Example 1, and the results are shown in Table 2.

Comparative Example 1

HPMC was produced in the same manner as in Example 1 except that the production conditions were changed as shown in Table 1. The various physical properties of the obtained HPMC were determined in the same manner as in Example 1, and the results are shown in Table 2.

Comparative Example 2

HPMC was produced in the same manner as in Example 3 except that the production conditions were changed as shown in Table 1. The various physical properties of the obtained HPMC were determined in the same manner as in Example 1, and the results are shown in Table 2.

Comparative Example 3

HPMC was produced in the same manner as in Example 3 except that the production conditions were changed as shown in Table 1. The various physical properties of the obtained HPMC were determined in the same manner as in Example 1, and the results are shown in Table 2.

TABLE 1

|  | granulated HPMC water content (wt %) | dried HPMC | | second wet HPMC | | HPMC | | |
|---|---|---|---|---|---|---|---|---|
|  |  | average particle diameter (mm) | water content (wt %) | water content (wt %) | staying time (min) | methoxy group (wt %) | hydroxy-propoxy group (wt %) | viscosity of 2 wt % aq. sol. (mPa·s) |
| Example 1 | 43.1 | 2.5 | 6 | 18 | 20 | 23.5 | 9.3 | 8,100 |
| Example 2 | 43.1 | 2.5 | 6 | 47 | 20 | 23.5 | 9.3 | 7,650 |
| Example 3 | 45.2 | 4.0 | 6 | 46 | 20 | 23.5 | 9.3 | 7,220 |
| Example 4 | 45.6 | 3.5 | 7 | 49 | 20 | 23.4 | 9.2 | 96,100 |
| Example 5 | 45.6 | 3.5 | 7 | 55 | 20 | 23.4 | 9.2 | 105,000 |
| Example 6 | 45.6 | 3.5 | 7 | 60 | 20 | 23.4 | 9.2 | 117,900 |
| Comp. Ex. 1 | 43.1 | 2.5 | 6 | 58 | 20 | 23.5 | 9.3 | 5,550 |
| Comp. Ex. 2 | 45.6 | 3.5 | 7 | 64 | 20 | 23.4 | 9.2 | 123,000 |
| Comp. Ex. 3 | 45.6 | 1.1 | 7 | 56 | 20 | 23.4 | 9.2 | 117,100 |

TABLE 2

|  | average particle diameter (μm) | specific surface area by BET (m$^2$/g) | volume fractions by QICPIC | | | | | | |
|---|---|---|---|---|---|---|---|---|---|
|  |  |  | fine particles (%) | spherical particles (%) | long fibrous particles A (%) | short fibrous particles B (%) | A + B (%) | B/A (—) | compressibility (N) |
| Example 1 | 79 | 0.41 | 0.8 | 38.6 | 33.6 | 26.9 | 60.6 | 0.80 | 277 |
| Example 2 | 69 | 0.42 | 1.0 | 49.2 | 23.0 | 26.8 | 49.8 | 1.17 | 235 |
| Example 3 | 72 | 0.46 | 1.3 | 44.5 | 27.0 | 27.2 | 54.2 | 1.01 | 251 |
| Example 4 | 77 | 0.49 | 0.9 | 45.1 | 32.5 | 21.5 | 54.0 | 0.66 | 293 |
| Example 5 | 69 | 0.47 | 1.1 | 43.0 | 32.4 | 23.6 | 56.0 | 0.73 | 236 |
| Example 6 | 77 | 0.48 | 0.8 | 54.0 | 27.9 | 17.3 | 45.2 | 0.62 | 258 |
| Comp. Ex. 1 | 85 | 0.33 | 0.3 | 75.5 | 12.6 | 11.5 | 24.1 | 0.91 | 121 |
| Comp. Ex. 2 | 72 | 0.40 | 1.3 | 68.1 | 14.9 | 15.6 | 30.5 | 1.05 | 173 |
| Comp. Ex. 3 | 66 | 0.47 | 2.4 | 53.0 | 21.7 | 22.9 | 44.6 | 1.06 | 241 |

The HPMCs obtained in Examples 1 to 6 showed a high compressibility of more than 200 N, while the HPMCs obtained in Comparative Examples 1 and 2 had poor compressibility.

Examples 7 to 12 and Comparative Examples 4 to 6

Sustained release tablets were produced by using the HPMCs obtained in Examples 1 to 6 and Comparative Examples 1 to 3 in the following procedures. The components except magnesium stearate in the following formulation were mixed in a polyethylene bag for 3 minutes. The resulting mixture was subjected to addition of magnesium stearate, and mixed for 30 seconds. Then the mixture was subjected to dry direct tableting in the following tableting conditions to obtain the sustained release tablets. The tablet weight, the tablet weight deviation (RSD: relative standard deviation) and the tablet hardness of the produced tablets were determined by using a tablet hardness tester (TM5-1, manufactured by KIKUSUI SEISAKUSHO LTD.) in the following conditions, and the results are shown in Table 3.

Figure 2:
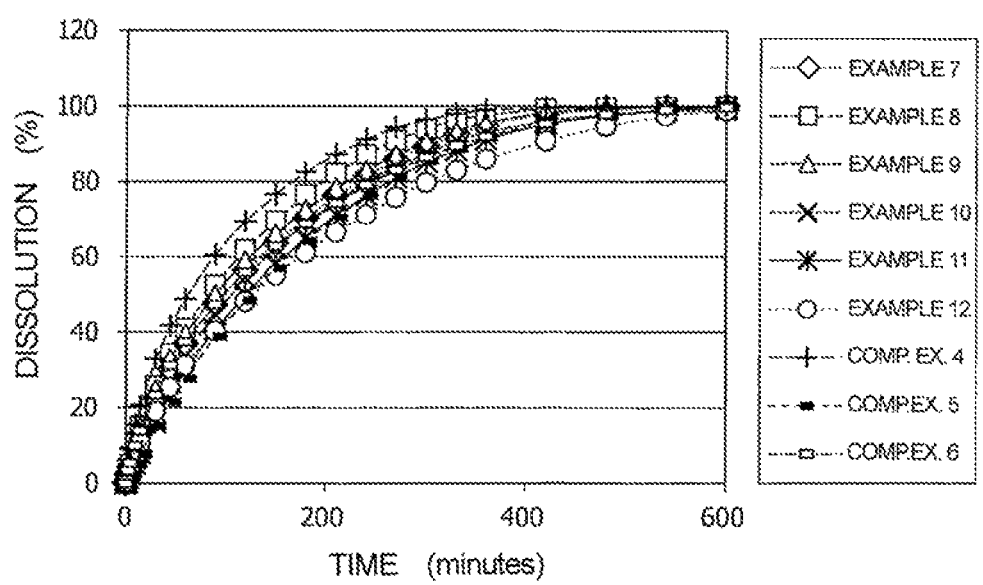
FIG. 2 shows dissolution profiles of acetaminophen from sustained-release tablets of Examples 7 to 12 and Comparative Examples 4 to 6.

The dissolution test of the produced sustained-release tablets was carried out with a dissolution tester (NTR-6400A, manufactured by Toyama Sangyo Co., Ltd.) in accordance with Dissolution Test (37° C., paddle method, 50 rpm, a solvent: 900 mL of purified water) described in the Japanese Pharmacopoeia Seventeenth Edition. The dissolution of acetaminophen after 1, 2, 4, and 8 hours are shown in Table 3, and the dissolution behavior of acetaminophen is shown in FIG. 2.

<Tablet Formulation and Tableting Conditions>
<Tablet Formulation>

| Acetaminophen fine powder (manufactured by Yamamoto Chemical Industry Co.): | 10.0 parts by weight |
|---|---|
| Lactose hydrate (Dilactose S, manufactured by Freund Corporation): | 70.0 parts by weight |
| HPMC: | 20.0 parts by weight |
| Magnesium stearate: | 0.5 part by weight |

<Tableting Conditions>
   Tableting machine: rotary tableting machine (VIRGO, manufactured by KIKUSUI SEISAKUSHO LTD.)
   Tablet size: 200 mg/tablet, a diameter of 8 mm, and a curved surface radius of 12 mm
   Tableting pressure: 7.5 kN
   Tableting speed: 40 rpm <Measurement of Tablet Physical Properties>
<Tablet Weight>
The weights of 20 tablets were measured with TM5-1, and the average was used as the tablet weight.
<Tablet Weight Deviation>
The tablet weight deviation was calculated in accordance with the following equation.

Tablet weight deviation (%) =(standard deviation of tablet weight/tablet weight)×100

<Tablet Hardness>
A load was applied to a tablet at a speed of 1 mm/sec in a diameter direction, and a maximum breaking strength at the time when the tablet was broken was measured as the tablet hardness.

TABLE 3

| | HPMC used | tablet weight (mg) | tablet weight deviation (%) | tablet hardness (N) | dissolution 1 hour later (%) | 2 hours later (%) | 4 hours later (%) | 8 hours later (%) |
|---|---|---|---|---|---|---|---|---|
| Example 7 | Example 1 | 200.9 | 0.54 | 61.1 | 37 | 56 | 81 | 99 |
| Example 8 | Example 2 | 200.6 | 0.56 | 54.9 | 41 | 62 | 87 | 100 |
| Example 9 | Example 3 | 201.7 | 0.59 | 58.6 | 39 | 59 | 83 | 99 |
| Example 10 | Example 4 | 200.6 | 0.67 | 63.1 | 34 | 54 | 80 | 98 |
| Example 11 | Example 5 | 200.1 | 0.84 | 63.0 | 29 | 50 | 76 | 98 |
| Example 12 | Example 6 | 201.0 | 0.60 | 52.1 | 31 | 48 | 71 | 95 |
| Comp. Ex. 4 | Comp. Ex. 1 | 200.8 | 0.45 | 36.2 | 49 | 69 | 91 | 100 |
| Comp. Ex. 5 | Comp. Ex. 2 | 201.4 | 0.39 | 44.3 | 28 | 48 | 76 | 97 |
| Comp. Ex. 6 | Comp. Ex. 3 | 201.0 | 1.17 | 56.8 | 37 | 56 | 79 | 98 |

The tablets obtained in Examples showed good tablet hardness of 50 N or more. In contrast, the tablets obtained in Comparative Examples 4 and 5 showed tablet hardness of 50 N or less, which was lower than those in Examples. The tablets obtained in Examples had a weight deviation of 1% or less, indicating good flowability. In contrast, the tablets obtained in Comparative Example 6 and produced by using the HPMC containing a large number of fine particles, had a large tablet weight deviation, indicating poor flowability.

It is evident from FIG. 2 that the dissolution profiles of acetaminophen from the sustained-release tablets obtained in Examples are of sustained release.

The invention claimed is:
1. A hydroxyalkyl alkyl cellulose comprising:
   a volume-based average particle diameter, determined by dry laser diffractometry, of 50 to 100 μm, and having, on a basis of a dynamic image analysis to divide all particles into fine particles, spherical particles and fibrous particles, a volume fraction of the fibrous particles consisting of long and short fibrous particles relative to all of the particles of 45 to 70%, and a volume fraction of the fine particles relative to all of the particles of less than 2.0%, wherein
   the fine particles have a length of fiber of less than 40 μm,
   the spherical particles have a length of fiber of 40 μm or more and consist of first and second spherical particles, wherein the first spherical particles have an elongation, which is a ratio of a diameter of fiber to a length of fiber, of 0.5 or more, and the second spherical particles have an elongation of less than 0.5, an aspect ratio, which is a ratio of a maximal Feret diameter to a minimal Feret diameter, of 0.5 or more, and a circularity, which is a ratio of a perimeter ($P_{EQPC}$) of a circle that has the same area as a projection area to a perimeter ($P_{real}$) of a real particle, of 0.7 or more, the long fibrous particles have a length of fiber of 200 μm or more and an elongation of less than 0.5, and consist of first and second long fibrous particles, wherein the first long fibrous particles have an aspect ratio of less than 0.5, and the second long fibrous particles have an aspect ratio of 0.5 or more and a circularity of less than 0.7, and the short fibrous particles have a length of fiber of 40 μm or more and less than 200 μm and an elongation of less than 0.5, and consist of first and second short fibrous particles wherein the first short fibrous particle have an aspect ratio of less than 0.5, and the second short fibrous particle have an aspect ratio of 0.5 or more and a circularity of less than 0.7.

2. The hydroxyalkyl alkyl cellulose according to claim 1, having a volume fraction of the short fibrous particles of 15 to 35%.

3. The hydroxyalkyl alkyl cellulose according to claim 1, having a volume fraction ratio of the short fibrous particles to the long fibrous particles of 0.60 to 1.40.

4. The hydroxyalkyl alkyl cellulose according to claim 1, having a specific surface area, determined by the BET method, of not less than 0.35 $m^2/g$ and less than 0.50 $m^2/g$.

5. The hydroxyalkyl alkyl cellulose according to claim 1, having such a viscosity that a 2% by weight aqueous solution of the hydroxyalkyl alkyl cellulose has a viscosity at 20° C. of 50 to 200,000 mPa·s.

6. The hydroxyalkyl alkyl cellulose according to claim 1, wherein the hydroxyalkyl alkyl cellulose is hydroxypropyl methyl cellulose.

7. A solid preparation comprising the hydroxyalkyl alkyl cellulose of claim 1.

8. The solid preparation according to claim 7, wherein the solid preparation is a sustained-release preparation.

9. A method for producing a hydroxyalkyl alkyl cellulose, comprising the steps of:

bringing cellulose pulp into contact with an alkali metal hydroxide solution to obtain alkali cellulose;

reacting the alkali cellulose with an etherifying agent to obtain a hydroxyalkyl alkyl cellulose product;

washing and draining the hydroxyalkyl alkyl cellulose product to obtain a first wet hydroxyalkyl alkyl cellulose;

granulating the first wet hydroxyalkyl alkyl cellulose to obtain a granulated hydroxyalkyl alkyl cellulose;

drying the granulated hydroxyalkyl alkyl cellulose to obtain a dried hydroxyalkyl alkyl cellulose having an average particle diameter, determined by a sieving analysis, of 2 to 10 mm and a water content of 6 to 10% by weight;

mixing the dried hydroxyalkyl alkyl cellulose with water to obtain a second wet hydroxyalkyl alkyl cellulose; and drying and pulverizing the second wet hydroxyalkyl alkyl cellulose to obtain a hydroxyalkyl alkyl cellulose of claim 1.

10. The method for producing a hydroxyalkyl alkyl cellulose according to claim 9, wherein the second wet hydroxyalkyl alkyl cellulose has a water content of more than 6% by weight and not more than 47% by weight, and a 2% by weight aqueous solution of the produced hydroxyalkyl alkyl cellulose has a viscosity at 20° C. of 50 to 10,000 mPa·s.

11. The method for producing a hydroxyalkyl alkyl cellulose according to claim 9, wherein the second wet hydroxyalkyl alkyl cellulose has a water content of more than 47% by weight and not more than 65% by weight, and a 2% by weight aqueous solution of the produced hydroxyalkyl alkyl cellulose has a viscosity at 20° C. of more than 10,000 mPa·s and not more than 200,000 mPa·s.

12. A method for producing a tablet, comprising:

each step in the method for producing a hydroxyalkyl alkyl cellulose according to claim 9; and a step of tableting the produced hydroxyalkyl alkyl cellulose by a dry direct tableting method or a dry granulation tableting method.

* * * * *